(12) United States Patent
Sutoris et al.

(10) Patent No.: US 6,379,588 B1
(45) Date of Patent: *Apr. 30, 2002

(54) STABILIZED MONOMER COMPOSITION

(75) Inventors: Heinz Friedrich Sutoris, Frankenthal; Andreas Koch, Bobenheim-Roxheim; Alexander Aumüller, Neustadt; Jacques Dupuis, Ludwigshafen; Manfred Niessner, Schifferstadt, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/269,165
(22) PCT Filed: Sep. 9, 1997
(86) PCT No.: PCT/EP97/04893
   § 371 Date: Mar. 23, 1999
   § 102(e) Date: Mar. 23, 1999
(87) PCT Pub. No.: WO98/13346
   PCT Pub. Date: Apr. 2, 1998

(30) Foreign Application Priority Data

Sep. 23, 1996  (DE) .......................................... 196 38 868

(51) Int. Cl.$^7$ .............................................. C09K 15/16
(52) U.S. Cl. ............. 252/405; 252/182.29; 252/182.12; 252/403; 252/404; 252/397; 585/3; 585/4; 585/5

(58) Field of Search ................ 585/5, 3, 4; 252/182.29, 252/183.12, 403, 404, 405, 397

(56) References Cited

U.S. PATENT DOCUMENTS

| 5,416,215 A | * | 5/1995 | Büschken et al. | 546/184 |
| 5,439,958 A | * | 8/1995 | Scrima et al. | 524/102 |
| 5,514,738 A | * | 5/1996 | Boratta et al. | 524/102 |
| 5,554,792 A | * | 9/1996 | Sawayama et al. | 564/4 |
| 6,143,205 A | * | 11/2000 | Sutoris et al. | 252/405 |

* cited by examiner

*Primary Examiner*—Jill Warden
*Assistant Examiner*—Monique T. Cole
(74) *Attorney, Agent, or Firm*—Oblon, Spivak, McClelland, Maier & Neustadt, P.C.

(57) ABSTRACT

A monomer composition, which contains
  A) vinyl-containing monomers in which a heteroatom selected from the group consisting of the halogens, nitrogen, oxygen, sulfur and silicon is present on the vinyl group, and
  B) a compound or a mixture of compounds of the formula II

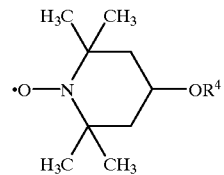

II where
  $R^4$ is methyl, ethyl, isopropyl, n-propyl, n-butyl, isobutyl, sec-butyl, tert-butyl or trimethylsilyl.

10 Claims, No Drawings

STABILIZED MONOMER COMPOSITION

BACKGROUND OF THE INVENTION

1. Field of the Invention

The present invention relates to monomer compositions containing

A) vinyl-containing monomers in which a heteroatom selected from the group consisting of the halogens, nitrogen, oxygen, sulfur and silicon is present on the vinyl group, and B) at least one N-oxyl compound of a secondary amine which carries no hydrogen atoms on the α-carbon atoms, in an amount effective as stabilizer for preventing premature polymerization.

2. Description of the Background

The present invention furthermore relates to processes for inhibiting the premature polymerization of vinyl-containing monomers and to the use of N-oxyl compounds of secondary amines which carry no hydrogen atoms on the α-carbon atoms as stabilizers for preventing premature polyemrization.

It is necessary to add stabilizers to the monomers in order to prevent premature polymerization. Sterically hindered amines, such as 2,2,6,6-tetraalkylpiperidine and derivatives thereof, including the N-oxyl derivatives, have proven particularly suitable for preventing free radical polymerizations.

U.S. Pat. No. 5,254,760 describes the stabilization of vinylaromatic compounds, such as styrene, during distillation and purification by a combination of at least one nitroxyl compound and at least one aromatic nitro compound. There is a danger here that traces of nitroxyl compounds will enter the purified monomers. However, even traces of nitroxyl compounds interfere with the subsequent polymerization; they cause delayed polymerization and uncontrolled chain terminations, leading to polymers having poor reproducibility and short chain lengths. These disadvantageous effects are described by Mardare et al. in Polym. Prep. (Am. Chem. Soc., Div. Polym. Sci.) 35 (1), (1994) 778.

For example, derivatives of phenylenediamine (U.S. Pat. No. 5,396,005), fullerenes (DE-A 44 14 773) or 2,6-di-tert-butyl-p-cresol (DE-A 43 28 950) have been used to date for stabilizing hetero-substituted vinyl compounds, such as N-vinylformamide or N-vinylpyrrolidone, during distillation and purification. However, these stabilizers are unsatisfactory with regard to their effectiveness.

SUMMARY OF THE INVENTION

It is an object of the present invention to provide monomer compositions which contain hetero-substituted vinyl compounds and suitable stabilizers, exhibit improved stabilization to premature polymerization and scarcely have any adverse effect on the subsequent specific polymerization of the monomers.

DETAILED DESCRIPTION OF THE PREFERRED EMBODIMENTS

We have found that this object is achieved by the monomer compositions stated at the outset.

The hetero-substituted vinyl monomers preferably carry a halogen, oxygen, nitrogen or sulfur as the heteroatom on the vinyl group.

Examples of suitable hetero-substituted vinylmonomers are vinyl halides, such as vinyl chloride, vinyl carboxylates, such as vinyl acetate, vinyl propionate or vinyl butyrate, vinyl ethers, such as methyl vinyl ether, ethyl vinyl ether or butyl vinyl ether, vinyl thioethers, vinylcarbazoles, vinylpyrrolidones, vinylphthalimides, vinyl isocyanates, vinylcaprolactams, vinylimidozoles, vinylformamide, vinylsulfonic acid and vinylsilanes, such as vinyltriacetoxysilane, vinyltrichlorosilane or vinyltrimethoxysilane.

Preferred monomer compositions contain

A) monomers of the general formula I

 I, where
X is oxygen or $-NR^2-$,
$R^1$ is

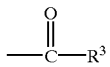

or $-R^3$, $R^2$ is hydrogen or $C_1$–$C_4$-alkyl or, together with $R^3$, is a saturated or unsaturated $C_3$-, $C_4$- or $C_5$-alkylene bridge in which one or two $CH_2$ groups may be replaced by NH, N($C_1$–$C_4$-alkyl), N($C_6$–$C_{10}$-aryl) or oxygen and one or two CH groups may be replaced by N, and $R^3$ is hydrogen, $C_1$–$C_4$-alkyl or a radical which, together with $R^2$, is a saturated or unsaturated $C_3$-, $C_4$- or $C_5$-alkylene bridge in which one or two $CH_2$ groups may be replaced by NH, N($C_1$–$C_4$-alkyl), N($C_6$–$C_{10}$-aryl) or oxygen and one or two CH groups may be replaced by N, and B) at least one N-oxyl compound of a secondary amine which carries no hydrogen atoms on the α-carbon atoms, in an amount effective as a stabilizer for preventing premature polymerization.

In the monomers (A) of the general formula I which are contained in the novel mixtures, X may be oxygen. Among these monomers, the vinyl ethers in which $R^1$ is $C_1$–$C_4$-alkyl, i.e. methyl, ethyl, n-propyl, iso-propyl, n-butyl, iso-butyl, sec-butyl or tert-butyl, are particularly suitable as a component of the novel monomer compositions.

If X is $-NR^2-$, $R^1$ is preferably $-CO-R^3$.

Other suitable radicals $R^3$ in addition to hydrogen and the stated $C_1$–$C_4$-alkyl groups are those radicals which, together with $-NR^2-$, form a saturated or unsaturated 5- to 7-membered ring. Examples of such ring systems are:

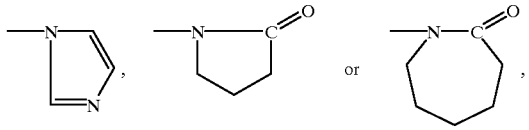

in particular the N-pyrrolidinonyl and the N-caprolactamyl radical.

Preferred monomers in the novel compositions are N-vinylformamide, N-vinyl-2-pyrrolidone, N-vinyl-ε-caprolactam and the abovementioned $C_1$–$C_4$-alkyl vinyl ethers.

Particularly preferred among these monomers is N-vinylformamide.

The novel monomer compositions contain, as stabilizers (B), at least one N-oxyl compound of a secondary amine which carries no hydrogen atoms on the α-carbon atoms.

These compounds may be present as free compounds or in the form of their salts.

Suitable N-oxyls of amines are, for example, the following structures

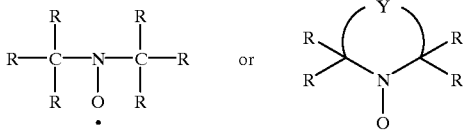

where R are identical or different alkyl, cycloalkyl, aralkyl or aryl radicals which may also be bonded in pairs to form a ring system, and Y is a group which is required to complete a 5- or 6-membered ring. For example, R is $C_1-C_{20}$-alkyl, in particular $C_1-C_8$-alkyl, $C_5$- or $C_6$-cycloalkyl, benzyl or phenyl. Y is, for example, alkylene $-(CH_2)_2-$ or $-(CH_2)_3-$.

N-Oxyl compounds such as the following structures

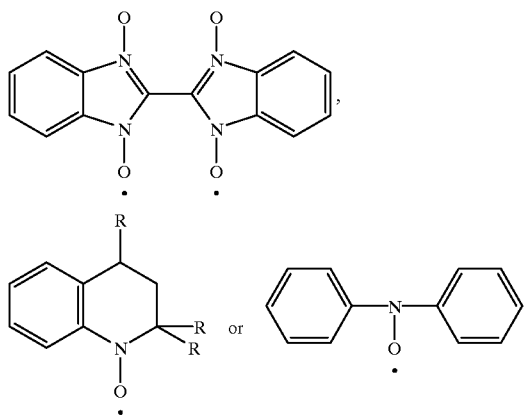

where the aromatic rings may each furthermore carry from 1 to 3 inert substituents, for example $C_1-C_4$-alkyl, $C_1-C_4$-alkoxy or cyano, are also suitable.

Sterically hindered derivatives of cyclic amines, for example of piperidine or pyrrolidine compounds, which may contain a further heteroatom, such as nitrogen, oxygen or sulfur, in the ring, are preferably used, this heteroatom not being adjacent to the hindered amine nitrogen. The steric hindrance is achieved by substituents in two positions adjacent to the amine nitrogen, suitable substituents being hydrocarbon radicals which replace all four hydrogen atoms of the $\alpha$-$CH_2$ groups. Examples of such substituents are phenyl, $C_3-C_6$-cycloalkyl, benzyl and in particular $C_1-C_6$-alkyl, where the alkyl radicals bonded to the same $\alpha$-carbon atom may furthermore be bonded to one another to form a 5- or 6-membered ring. The radicals mentioned specifically under $R^4$ and $R^5$ are particularly preferred. Preferably used N-oxyls of sterically hindered amines are derivatives of 2,2,6,6-tetraalkylpiperidine.

Preferred N-oxyl compounds in the novel monomer compositions are those of the general formula II

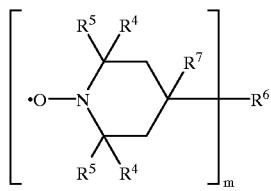

where
$R^4$ and $R^5$ are each $C_1-C_4$-alkyl or phenyl or, together with the carbon atom to which they are bonded, are a 5- or 6-membered saturated hydrocarbon ring, $R^6$ is hydrogen, hydroxyl, amino or an m-valent organic radical bonded via oxygen or nitrogen or, together with $R^7$ is oxygen or a ring structure defined under $R^7$, $R^7$ is hydrogen or $C_1-C_{12}$-alkyl or, together with $R^6$ is oxygen or, together with $R^6$ and the carbon atom to which they are bonded, is one of the following ring structures

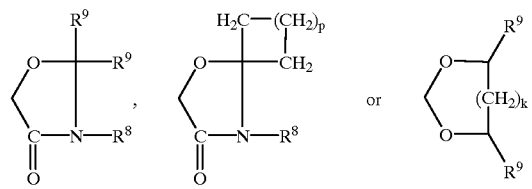

where, when $R^6$ forms a common radical with $R^7$; m is 1, $R^8$ is hydrogen, $C_1-C_{12}$-alkyl or $-(CH_2)_z-COOR^9$, $R^9$ are identical or different $C_1-C_{18}$-alkyl radicals, k is 0 or 1, z and p are each from 1 to 12 and m is from 1 to 100.

$R^4$ and $R^5$ may be, for example, the $C_1-C_4$-alkyl groups stated for $R^1$ or together they may form a tetra- or pentamethylene group. $R^4$ and $R^5$ are each preferably methyl.

Examples of suitable radicals $R^7$ are hydrogen, the abovementioned $C_1-C_4$-alkyl groups and pentyl, sec-pentyl, tert-pentyl, neopentyl, hexyl, 2-methylpentyl, heptyl, 2-methylhexyl, octyl, isooctyl, 2-ethylhexyl, nonyl, 2-methylnonyl, isononyl, 2-methyloctyl, decyl, isodecyl, 2-methylnonyl, undecyl, isoundecyl, dodecyl and isododecyl, (the names isooctyl, isononyl and isodecyl are trivial names and originate from the carbonyl compounds obtained by the oxo synthesis; in this context, cf. Ullmann's Encyclopedia of Industrial Chemistry, 5th Edition, Vol. A1, pages 290–293, and Vol. A10, pages 284 and 285).

p is preferably 6–12, particularly preferably 9.

z is preferably 1–4, particularly preferably 2.

Suitable radicals $R^8$ in addition to hydrogen are, for example, the abovementioned $C_1-C_{12}$-alkyl groups. $R^8$ is preferably hydrogen, $C_1-C_4$-alkyl or $(CH_2)_z-COO(C_1-C_6$-alkyl), particularly preferably $-CH_2-CH_2-COO(CH_2)_{11}-CH_3$ and $-CH_2-CH_2-COO(CH_2)_{13}-CH_3$.

$R^9$ may be, for example, one of the abovementioned $C_1-C_{12}$-alkyl groups or tridecyl, isotridecyl, tetradecyl, pentadecyl, hexadecyl, heptadecyl or octadecyl. Dodecyl and hexadecyl are preferred.

Preferred radicals $R^6$ are, for example, the following m-valent radicals

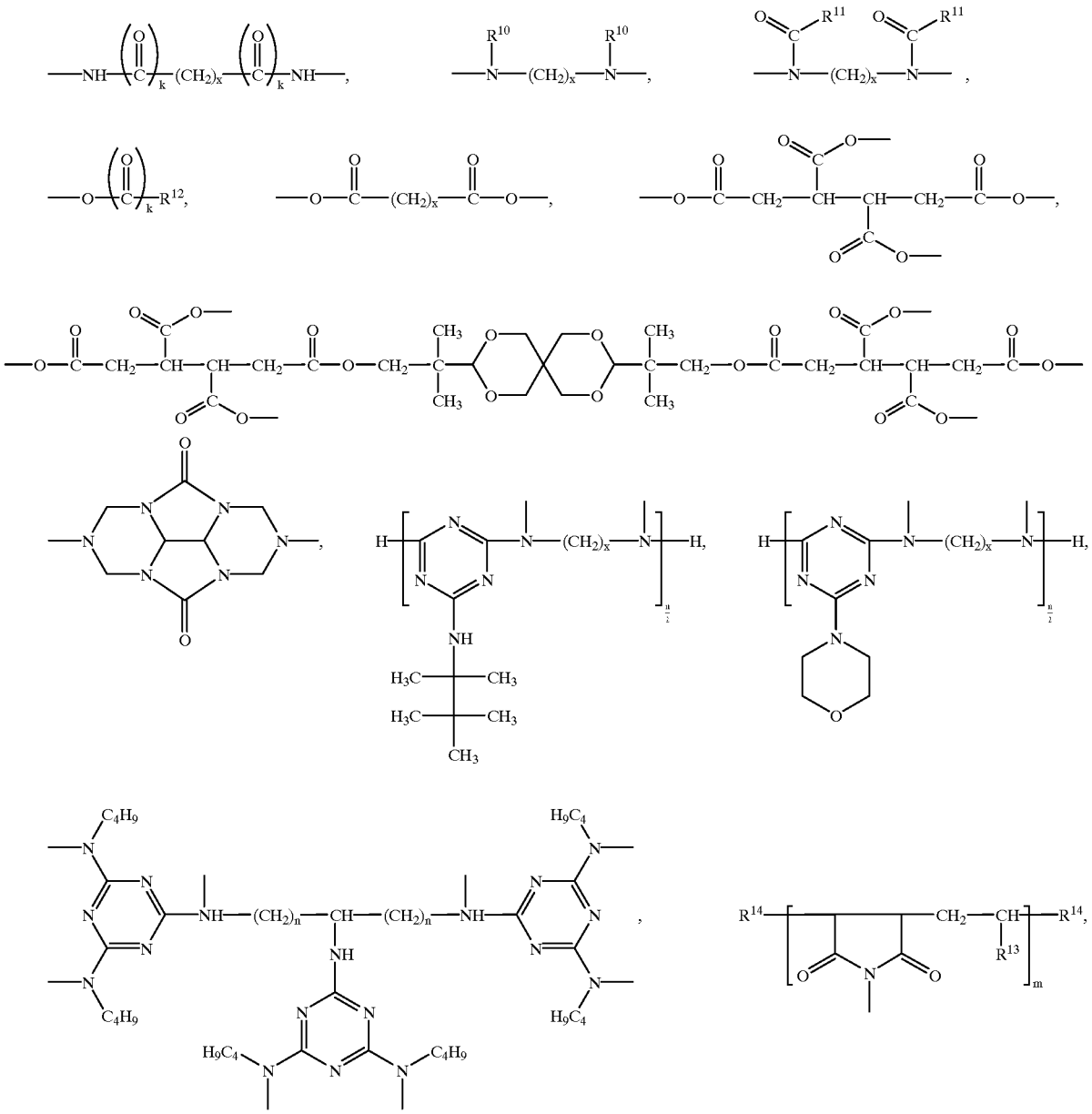

where
- $R^{10}$ is $C_1$–$C_{12}$-alkyl or —$(CH_2)_z$—$COOR^9$,
- $R^{11}$ is hydrogen or $C_1$–$C_{18}$-alkyl,
- $R^{12}$ is $C_1$–$C_{18}$-alkyl, vinyl or isopropenyl,
- $R^{13}$ is $C_8$–$C_{22}$-alkyl,
- $R^{14}$ is hydrogen or an organic radical as usually formed in the free radical polymerization of the starting monomers,
- k is 0 or 1,
- x is from 1 to 12 and
- n is an even number m.

If $R^6$ is one of these radicals, $R^7$ is preferably hydrogen. m may then be from 1 to 100. m is preferably 1, 2, 3, 4 or from 10 to 50, mixtures generally being used particularly in the case of the oligomeric or polymeric radicals $R^6$.

Suitable radicals $R^{10}$ are those radicals stated for $R^8$. $R^{10}$ is preferably $C_1$–$C_4$-alkyl.

Suitable radicals $R^{11}$ in addition to hydrogen are those radicals which have been stated for $R^9$. $R^{11}$ is preferably hydrogen.

Particularly suitable radicals $R^{12}$ are vinyl, isopropenyl and $C_{15}$–$C_{17}$-alkyl.

Examples of suitable radicals $R^{13}$ are the abovementioned $C_8$–$C_{18}$-alkyl radicals and nonadecyl, eicosyl, uneicosyl and doeiosyl. Mixtures of different radicals $R^{13}$ which differ in the length of the carbon chain are preferred.

$R^{14}$ is hydrogen or an organic radical as formed in the free radial polymerization of the starting monomers, in this case of an ethylene derivative and a maleimide derivative, i.e. a radical which is formed from the polymerization initiator or from an intermediate radical, or another radical of this type which is familiar to the person skilled in the art.

Other preferred stabilizers in the novel monomer compositions are compounds or mixtures of compounds of the general formula IIa

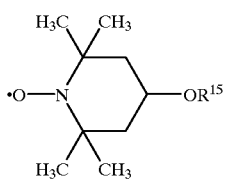

where $R^{15}$ is methyl, ethyl, isopropyl, n-propyl, n-butyl, isobutyl, sec-butyl, tert-butyl, fluorine, chlorine or trimethylsilyl. The stabilizers of the formula IIa are particularly suitable for monomer compositions which are to be purified by distillation.

Preferred nitroxyl compounds as component B) of the novel monomer compositions are also the following:

1-oxyl-2,2,6,6-tetramethylpiperidine,
1-oxyl-2,2,6,6-tetramethylpiperidin-4-ol,
1-oxyl-2,2,6,6-tetramethylpiperidin-4-one,
1-oxyl-2,2,6,6-tetramethylpiperidin-4-yl acetate,
1-oxyl-2,2,6,6-tetramethylpiperidin-4-yl 2-ethylhexanoate,
1-oxyl-2,2,6,6-tetramethylpiperidin-4-yl stearate,
1-oxyl-2,2,6,6-tetramethylpiperidin-4-yl benzoate,
1-oxyl-2,2,6,6-tetramethylpiperidin-4-yl 4-tert-butylbenzoate,
bis (1-oxyl-2,2,6,6-tetramethylpiperidin-4-yl)succinate,
bis (1-oxyl-2,2,6,6-tetramethylpiperidin-4-yl)adipate,
bis (1-oxyl-2,2,6,6-tetramethylpiperidin-4-yl)sebacate,
bis (1-oxyl-2,2,6,6-tetramethylpiperidin-4-yl)n-butylmalonate,
bis (1-oxyl-2,2,6,6-tetramethylpiperidin-4-yl)phthalate,
bis (1-oxyl-2,2,6,6-tetramethylpiperidin-4-yl)isophthalate,
bis (1-oxyl-2,2,6,6-tetramethylpiperidin-4-yl)terephthalate,
bis (1-oxyl-2,2,6,6-tetramethylpiperidin-4-yl) hexyhydroterephthalate,
N,N'-bis-(1-oxyl-2,2,6,6-tetramethylpiperidin-4-yl)-N,N'-bisformyl,-1,6-diaminohexane
N,N'-bis(1-oxyl-2,2,6,6-tetramethylpiperidin-4-yl) adipinamide,
N-(1-oxyl-2,2,6,6-tetramethylpiperidin-4-yl)caprolactam,
N-(1-oxyl-2,2,6,6-tetramethylpiperidin-4-yl) dodecylsuccinimide,
2,4,6-tris-[N-butyl-N-(1-oxyl-2,2,6,6-tetramethylpiperidin-4-yl]-s-triazine,
4,4'-ethylenebis(1-oxyl-2,2,6,6-tetramethylpiperazin-3-one) and
tris(2,2,6,6-tetramethyl-1-oxyl-piperidin-4-yl)phosphite.

The nitroxyl compounds described can be prepared from the corresponding piperidine compounds by oxidation, for example with hydrogen peroxide. Details of this oxidation are given, for example, in the prior German Patent Application 195 101 84.7. The secondary amine which carry no hydrogen atoms on the α-carbon atoms, such as piperidine compounds, and their preparation are generally known. Since the oxidation reactions do not always go to completion, the piperidine compounds used as starting compounds as well as partially oxidized intermediates may be present in the novel monomer compositions.

Particularly suitable monomer compositions are those which contain one or more aromatic nitroso or nitro compounds in addition to the stated nitroxyl compounds for stabilization.

For example, 1,3-dinitrobenzene, 1,4-dinitrobenzene, 2,6-dinitro-4-methylphenol, 2-nitro-4-methylphenol, 2,4,6-trinitrophenol, 2,4-dinitro-1-naphthol, 2,4-dinitro-6-methylphenol, 2,4-dinitrochlorobenzene, 2,4-dinitrophenol, 2,4-dinitro-6-sec-butylphenol, 4-cyano-2-nitrophenol, 3-iodo-4-cyano-5-nitrophenol, particularly preferably 2,6-dinitro-4-methylphenol, 2-nitro-4-methylphenol, 2,4-dinitro-6-sec-butylphenol and 2,4-dinitro-6-methylphenol may be used as aromatic nitro compounds.

Examples of suitable aromatic nitroso compounds are p-nitrosophenol, p-nitroso-o-kresol and p-nitroso-N,N'-diethylaniline.

Furthermore, substituted phenols may also be added to the monomer compositions as costabilizers, for example the following substituted phenols:

4-tert-butylpyrocatechol, methoxyhydroquinone, 2,6-di-tert-butyl-4-methylphenol, n-octadecyl β-(3,5-di-tert-butyl-4-hydroxy-phenol)propionate, 1,1,3-tris(2-methyl-4-hydroxy-5-tert-butylphenol)butane, 1,3,5-trimethyl-2,4,6-tris(3,5-di-tert-butyl-4-hydroxybenzyl)benzene, 1,3,5-tris(3,5-di-tert-butyl-4-hydroxybenzyl) isocyanurate, 1,3,5-tris[β-(3,5-di-tert-butyl-4-hydroxyphenyl)propionyloxyethyl] isocyanurate, 1,3,5-tris(2,6-dimethyl-3-hydroxy-4-tert-butylbenzyl)isocyanurate and pentaerythrityl tetrakis[β-(3,5-di-tert-butyl-4-hydroxy-phenyl)propionate].

The novel monomer compositions may furthermore contain one or more costabilizers selected from the group consisting of the phenothiazines, quinones, hydroxylamines and phenyldiamines.

For the stabilization of the novel monomer compositions, the latter contain in general from 0.0002 to 5, preferably from 0.0005 to 0.5, % by weight, based on the total amount of the monomer composition, of the nitroxyl compounds.

The stabilizers display their stabilizing effect in a broad temperature range. They are effective at any conventional storage temperature from −50 to +50° C. and also at elevated temperatures, as used, for example, in the distillation of the monomers. The pressure range of the stabilization process is also not critical. The stabilizers are effective at atmospheric pressure and also at reduced pressure, as used in some distillation processes.

The novel process for inhibiting the premature polymerization of monomers is used during the preparation, the distillation or the purification of the monomers and also during their storage and transport. Particularly in the distillation, the use of small N-oxyl compounds which, during the distillation, have a sufficient vapor pressure to display their action in the vapor space as well is particularly advantageous. The N-oxyl compounds of the formula IIa are particularly suitable for this purpose.

EXAMPLE

Storage of N-vinylformamide in the presence of N,N'-bis (1-oxyl-2,2,6,6-tetramethylpiperidin-4-yl)-N,N'-bis-formyl-1,6-diaminohexane A monomer composition comprising vinylformamide and 0.05% by weight, based on the total amount of the composition, of N,N'-bis(1-oxyl-2,2,6,6-tetramethylpiperidin-4-yl)-N,N'-bis-formyl-1,6-diaminohexane was stored at 40° C. After the times stated in the table, a sample was taken and the vinylformamide content was determined by iodometric titration. The iodine numbers determined are shown in the table as a measure of the respective vinylformamide content.

| Storage time [Days] | Iodine number without stabilizer | Iodine number with stabilizer |
| --- | --- | --- |
| 0 | 98.8 | 98.2 |
| 20 | 89.9 | 92.8 |
| 41 | 80.5 | 87.5 |
| 62 | 71.5 | 81.2 |
| 83 | 62.5 | 75.7 |

B) one or more compounds of the formula (II):

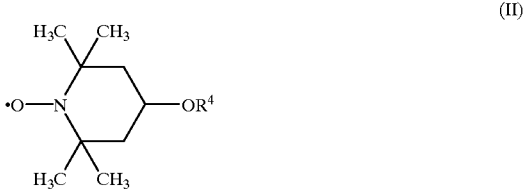

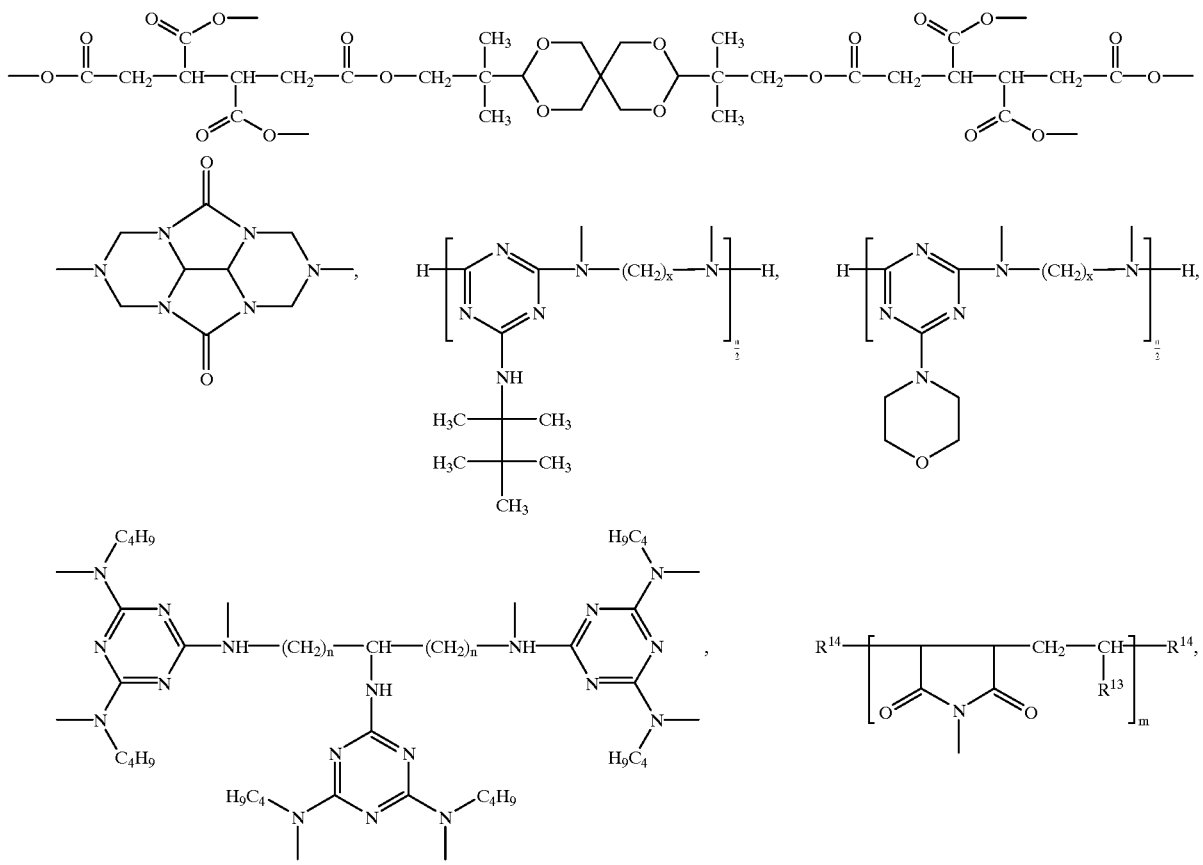

where $R^{10}$ is $C_1$–$C_{12}$-alkyl or —$(CH_2)_z$—$COOR^9$, $R^{11}$ is hydrogen or $C_1$–$C_{18}$-alkyl, $R^{12}$ is $C_1$–$C_{18}$-alkyl, vinyl or isopropenyl, $R^{13}$ is $C_8$–$C_{22}$-alkyl, $R^{14}$ is hydrogen or an organic radical as usually formed in the free radical polymerization of the starting monomers, k is 0 or 1, x is from 1 to 12 and n is an even number m.

We claim:

1. A monomer composition, comprising:

A) one or more vinyl-containing monomers in which a heteroatom selected from the group consisting of halogen, nitrogen, oxygen, sulfur, and silicon is present on the vinyl group; and wherein $R^4$ is methyl, ethyl, isopropyl, n-propyl, n-butyl, isobutyl, sec-butyl, tert-butyl or trimethylsilyl.

2. The monomer composition of claim 1, wherein said one or more vinyl-containing monomers have the formula (I):

wherein:

X is oxygen or —$NR^2$—;

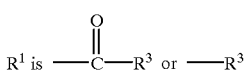

$R^2$ is hydrogen or $C_1$–$C_4$-alkyl or, together with $R^3$, is a saturated or unsaturated $C_3$-, $C_4$- or $C_5$-alkylene bridge in which one or two $CH_2$ groups are optionally replaced by NH, N($C_1$–$C_4$-alkyl), N($C_6$–$C_{10}$-aryl) or oxygen and one or two CH groups are optionally replaced by N; and $R^3$ is hydrogen, $C_1$–$C_4$-alkyl or a radical which, together with $R^2$, is a saturated or unsaturated $C_3$-, $C_4$- or $C_5$-alkylene bridge in which one or two $CH_2$ groups are optionally replaced by NH, N($C_1$–$C_4$-alkyl), N($C_6$–$C_{10}$-aryl) or oxygen and one or two CH groups are optionally replaced by N.

3. The monomer composition of claim 1, wherein said one or more vinyl-containing monomers is selected from the group consisting of N-vinylformamide, N-vinylpyrrolidone, N-vinylcaprolactam, vinyl chloride, or $C_1$–$C_4$-alkyl vinyl ether.

4. The monomer composition of claim 3, wherein said one or more vinyl-containing monomers is N-vinylformamide.

5. The monomer composition of claim 3, wherein said one or more vinyl-containing monomers is vinyl chloride.

6. The monomer composition of claim 1, which further comprises one or more aromatic nitroso or nitro compounds.

7. The monomer composition of claim 1, which further comprises one or more costabilizers selected from the group consisting of phenothiazines, quinones, hydroquinones and the ethers thereof, hydroxylamines, and phenylenediamines.

8. A process for inhibiting premature polymerization of one or more vinyl-containing monomers in which a heteroatom selected from the group consisting of halogen, nitrogen, oxygen, sulfur, and silicon is present on the vinyl group, which comprises adding at least one N-oxyl compound of the formula (II):

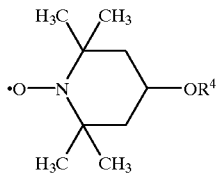

(II)

wherein:

$R^4$ is methyl, ethyl, isopropyl, n-propyl, n-butyl, isobutyl, sec-butyl or trimethylsilyl, to the one or more vinyl-containing monomers in an amount effective as a stabilizer.

9. The process of claim 8, wherein said one or more vinyl-containing monomers is selected from the group consisting of N-vinylformamide, N-vinylpyrrolidone, N-vinylcaprolactam, and $C_1$–$C_4$-alkyl vinyl ether.

10. The process of claim 8, wherein the N-oxyl compound of the formula (II) is incorporated in said one or more vinyl-containing monomers in an amount of from about 0.0002 to 5% by weight based on the total amount of the one or more monomers.

* * * * *